(12) United States Patent
Noguchi et al.

(10) Patent No.: US 10,190,233 B2
(45) Date of Patent: Jan. 29, 2019

(54) METHOD AND DEVICE FOR PRODUCING A GROUP 13 ELEMENT NITRIDE CRYSTAL USING A SHIELDING OBJECT

(71) Applicant: NGK INSULATORS, LTD., Nagoya, Aichi-prefecture (JP)

(72) Inventors: Suguru Noguchi, Nagoya (JP); Shuhei Higashihara, Nagoya (JP); Takayuki Hirao, Nagoya (JP); Tetsuya Uchikawa, Nagoya (JP)

(73) Assignee: NGK INSULATORS, LTD., Aichi-prefecture (JP)

( * ) Notice: Subject to any disclaimer, the term of this patent is extended or adjusted under 35 U.S.C. 154(b) by 0 days.

(21) Appl. No.: 15/629,858

(22) Filed: Jun. 22, 2017

(65) Prior Publication Data

US 2017/0283983 A1    Oct. 5, 2017

Related U.S. Application Data

(63) Continuation of application No. PCT/JP2015/085055, filed on Dec. 15, 2015.

(30) Foreign Application Priority Data

Dec. 26, 2014  (JP) .................................. 2014-264368

(51) Int. Cl.
  *C30B 19/06* (2006.01)
  *C30B 23/00* (2006.01)
  (Continued)

(52) U.S. Cl.
  CPC .............. *C30B 23/005* (2013.01); *C07F 5/00* (2013.01); *C30B 19/02* (2013.01); *C30B 23/025* (2013.01); *C30B 23/06* (2013.01); *C30B 29/406* (2013.01)

(58) Field of Classification Search
  CPC .... C30B 9/00; C30B 9/04; C30B 9/08; C30B 9/10; C30B 19/00; C30B 19/02;
  (Continued)

(56) References Cited

U.S. PATENT DOCUMENTS 8,187,507 B2   5/2012  Mori et al.
8,574,361 B2  11/2013  Yamada et al.
(Continued)

FOREIGN PATENT DOCUMENTS

JP   2008-222519 A   9/2008
JP      4538596 B2   7/2010
(Continued)

OTHER PUBLICATIONS

International Search Report and Written Opinion for PCT Patent App. No. PCT/JP2015/085055 (dated Feb. 9, 2016) with English translation of the ISR.
English translation of the International Preliminary Report on Patentability for PCT Patent App. No. PCT/JP2015/085055 (dated Jul. 6, 2017).

*Primary Examiner* — Kenneth A Bratland, Jr.
(74) *Attorney, Agent, or Firm* — Cermak Nakajima & McGowan LLP; Tomoko Nakajima

(57) ABSTRACT

A group 13 element source, a flux comprising at least one of an alkali metal and an alkaline earth metal, and an additive being liquid at an ambient temperature are placed in a crystal growing vessel. The crystal growing vessel is heated and pressurized under a nitrogen atom-containing gas atmosphere to form a melt containing the group 13 element source, the flux and the additive. Evaporation of the additive is prevented until the flux is melted. The crystal of the nitride of the group 13 element is then grown in the melt.

11 Claims, 6 Drawing Sheets

(51) Int. Cl.
*C07F 5/00* (2006.01)
*C30B 23/02* (2006.01)
*C30B 23/06* (2006.01)
*C30B 19/02* (2006.01)
*C30B 29/40* (2006.01)

(58) Field of Classification Search
CPC ....... C30B 19/06; C30B 19/067; C30B 19/10; C30B 19/106; C30B 23/005; C30B 23/025; C30B 23/06; C30B 29/00; C30B 29/10; C30B 29/40; C30B 29/403; C30B 29/406; C07F 5/00; Y10T 117/00; Y10T 117/10; Y10T 117/1016; Y10T 117/1024; Y10T 117/1096
USPC ......... 117/11, 54, 64, 65, 67, 73, 77–79, 84, 117/109, 200, 204, 206, 224, 937, 952
See application file for complete search history.

(56) References Cited

U.S. PATENT DOCUMENTS

| | | |
|---|---|---|
| 9,090,988 B2 | 7/2015 | Sakai et al. |
| 2001/0015167 A1* | 8/2001 | Weber .................... C30B 15/04 117/11 |
| 2012/0168695 A2* | 7/2012 | Yamada .................... C30B 9/10 252/521.5 |

FOREIGN PATENT DOCUMENTS

| | | |
|---|---|---|
| JP | 4821007 B2 | 9/2011 |
| WO | WO2013/147326 A1 | 10/2013 |

* cited by examiner

METHOD AND DEVICE FOR PRODUCING A GROUP 13 ELEMENT NITRIDE CRYSTAL USING A SHIELDING OBJECT

TECHNICAL FIELD

The present invention relates to a method and apparatus for growing group 13 element nitride crystals. The group 13 element crystals can be applied, for example, to technical fields requiring high quality, more specifically, a white LED with high color rendering properties expected to be the next-generation light source that can substitute for a fluorescent lamp, a blue-violet laser for a high-speed and high-density optical memory, a LED headlight, a power device used in an inverter for a hybrid vehicle, and the like.

BACKGROUND ART

The flux method is one of the liquid phase methods. For gallium nitride, the use of sodium metal as a flux can significantly lower the temperature and pressure required for the crystal growth of gallium nitride. Specifically, nitrogen gas is dissolved in a mixed melt of sodium metal and gallium metal to bring gallium nitride into a supersaturated state, so that gallium nitride grows as crystals. In such liquid phase methods, dislocation hardly occurs as compared with the vapor phase methods, thereby high-quality gallium nitride having a low dislocation density can be obtained.

For example, in a method in which gallium nitride crystals are grown in the melt containing an alkali metal-containing flux and gallium, a crystal growth rate is slower than that in the vapor phase methods. When the high temperature/high pressure conditions are applied to increase the crystal growth rate in the flux method, a supersaturation degree of nitrogen in the flux is increased, thereby causing non-uniform nucleation (miscellaneous crystals) at the gas-liquid interface and resulting in deterioration of the crystals. Thus, it has been difficult to increase the crystal growth rate more than a certain degree.

It has been proposed that a hydrocarbon having the boiling point higher than the melting point of the alkali metal is added to the melt in order to suppress the occurrence of the miscellaneous crystals during the growth of the crystals and make uniform the thickness of the crystal film (Patent document 1: JP 4821007B). Further, the document mentions that the hydrocarbon added to the melt is preferably liquid from the standpoint of preventing the oxidation of the alkali metal by coating its surface and easiness in weighing.

Further, Patent document 2 (JP 4538596B) proposes that carbon that generates cyanide (CN) in the melt is added to the melt in order to suppress the miscellaneous crystals in the melt.

Further, the present inventors disclosed that the conductivity of crystals to be grown was controlled by using liquid dopants (Patent document 3). However, it became clear that this method was inadequate for controlling the dopant concentration in each growth batch.

Patent Documents

PATENT DOCUMENT 1: JP 4821007B
PATENT DOCUMENT 2: JP 4538596B
PATENT DOCUMENT 3: WO 2013-147326 A1

SUMMARY OF THE INVENTION

The method in Patent document 1 is effective in suppressing the miscellaneous crystal, however, it becomes clear that this method causes variation in the crystal growth rate with low reproducibility. Further, it also becomes clear that, when a template substrate is produced by depositing a group 13 element nitride crystal film on a seed crystal substrate, cracks are often generated due to a thermal expansion difference between the seed crystal substrate and the group 13 element nitride crystal, thereby resulting in reduction in the yield.

An object of the present invention is to provide a method of forming a melt containing a group 13 element source, a flux and an additive being liquid at an ambient temperature in a crystal growing vessel and of growing a group 13 element nitride crystal in the melt, in which the variation in the crystal growth can be reduced.

The present invention provides a method of producing a crystal of a nitride of a group 13 element: said method comprising:

placing a group 13 element source, a flux comprising at least one of an alkali metal and an alkaline earth metal and an additive being liquid at an ambient temperature in a crystal growing vessel; and heating and pressurizing said crystal growing vessel under a nitrogen atom-containing gas atmosphere to form a melt containing the group 13 element source, the flux and the additive, wherein evaporation of the additive is prevented until the flux is melted and then the crystal of the nitride of the group 13 element is grown in the melt.

Further, the present invention provides a crystal growth apparatus of growing a crystal of a nitride of a group 13 element, wherein a group 13 element source, a flux comprising at least one of an alkali metal and an alkaline earth metal and an additive being liquid at an ambient temperature are placed in a crystal growing vessel; and wherein the crystal growing vessel is heated and pressurized under a nitrogen atom-containing gas atmosphere to form a melt containing the group 13 element source, the flux and the additive to grow the crystal of the nitride of the group 13 element in the melt, the apparatus comprising an evaporation preventing means for preventing evaporation of the additive until the flux is melted at the time of heating and pressurizing the crystal growing vessel.

As a result of further studies on the above-mentioned problem, the present inventors made the following findings. Specifically, when the additive being liquid at an ambient temperature is added to the materials to be melted, the amount of the additive is adjusted, for example, by performing vacuum exhaustion after the addition of the additive. It was found that, in this manner, when the additive being liquid at an ambient temperature was added to the materials to be melted, it was evaporated between the material preparation and the crystal growth, thereby causing variation in an actual amount of the additive added to the melt. It is noted that the actual amount of the additive added to the melt is an amount of the additive obtained by subtracting the evaporation amount of the additive from the amount of the liquid additive added to the vessel. Further, the actual amount of the additive added to the melt changes depending on how the additive being liquid at an ambient temperature wets and spreads after applied and by the ambient humidity and temperature. This caused poor reproducibility in the action of the additive and made it difficult to reduce the variation in the crystal growth.

Consequently, it was found that variation, for example, in the crystal growth rate and the dopant concentration in each lot of the crystals caused a reduction in the yield.

Regarding this problem, it has been found that providing an evaporation preventing means that prevents evaporation of the additive until the flux is melted at the time of heating and pressurizing the crystal growing vessel enables to reduce variation in the crystal growth. For example, it has been found that, when the group 13 element nitride crystals are deposited on the seed crystal substrate, the cracks caused by the thermal expansion difference and variation in the thickness of the crystals between the two are reduced and the yield is improved accordingly. Further, it has been found that variation in the dopant concentration of the group 13 element nitride crystals is reduced and the yield is improved accordingly.

Figure 1A:
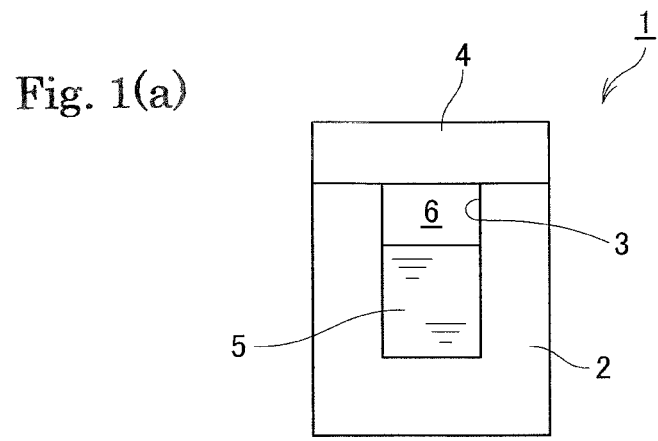
FIG. 1 (a) is a cross-section view schematically illustrating a container 1.
FIGS. 1(b) and 1(c) are perspective views schematically illustrating container main bodies 2 and 2A, respectively.

EMBODIMENTS FOR CARRYING OUT THE INVENTION (Group 13 Element Nitride Crystals)

The group 13 element refers to a group 13 element in the periodic table determined by IUPAC. Specific examples of the group 13 element include gallium, aluminum, indium, thallium, and the like. As the group 13 element nitride, gallium nitride, aluminum nitride, and gallium aluminum nitride are particularly preferable.

(Materials to be Melted)

As materials to be melted, a group 13 element source, a flux made of at least one of alkali metal and alkaline earth metal, and an additive being liquid at an ambient temperature are placed in a crystal growing vessel.

The group 13 element source is a raw material that generates group 13 element metal in a melt. As the raw material, simple metal of the group 13 element, an alloy containing the group 13 element, or a compound of the group 13 element may be applied, however, the simple metal of the group 13 element is preferable from the standpoint of handling.

Alkali metal constituting a flux includes lithium (Li), sodium (Na), potassium (K), rubidium (Rb), cesium (Cs), and francium (Fr). Of these, sodium (Na) is particularly preferable. One type of the alkali metal may be solely used, or two or more types thereof may be used in combination. Further, alkaline earth metal may be used as a component of the flux. Examples of the alkaline earth metal include Mg, Ca, Sr, and Ba.

The materials to be melted may further include a dopant. Examples of an n-type dopant include Si, Ge, Sn, and O, while examples of a p-type dopant include Zn.

In the present invention, an additive being liquid at an ambient temperature (25° C.) is further stored in the crystal growing vessel. As such an additive, a hydrocarbon and a germanium compound can be exemplified.

Regarding this point, Patent document 1 describes that the boiling point of the hydrocarbon needs to be higher than the melting point of the flux, otherwise the hydrocarbon is evaporated in the step of heating the crystal growing vessel to form the melt. However, in the present invention, a means that prevents evaporation of the additive is used before the flux is melted, thus the boiling point of the additive does not need to be higher than the melting point of the flux, that is, the boiling point of the additive may be equal to or lower than the melting point of the flux. This allows to use the additive having the low boiling point.

It is noted that, when two or more types of the flux is used, the flux having the lowest melting point is used as a reference. In this context, "the boiling point of the additive being higher than the melting point of the flux" means that the boiling point of the additive is higher than the melting point of the flux having the lowest melting point. Likewise, "the boiling point of the additive being equal to or lower than the melting point of the flux" means that the boiling point of the additive is equal to or lower than the melting point of the flux having the lowest melting point.

The melting points of Na, Li, and Ca are 98° C., 180° C., and 840° C., respectively.

It is preferred that the hydrocarbon does not contain a hetero atom, such as oxygen and sulfur, and is consisting of only a carbon atom and a hydrogen atom. Further, the hydrocarbon is preferably a chain saturated hydrocarbon, a chain unsaturated hydrocarbon, an alicyclic saturated hydrocarbon, an alicyclic unsaturated hydrocarbon, an aromatic hydrocarbon, or a mixture thereof.

Specific examples of the usable hydrocarbon having the boiling point higher than the melting point of sodium include kerosene, paraffin (e.g., heptadecane, octadecane, nonadecane, icosane, triacontane, vaseline, liquid paraffin), lamp oil, biphenyl, o-xylene, m-xylene, p-xylene, cumene, ethyl toluene, cymene, tetralin, cycloheptane, cyclooctane, cyclononane and cyclodecane. One type thereof may be solely used, or two or more types thereof may be used in combination.

Further, examples of the usable hydrocarbon having the boiling point equal to or lower than the melting point of sodium include pentane, hexane, cyclobutane, cyclopentane, cyclohexane, cyclohexene, and benzene. One type thereof may be solely used, or two or more types thereof may be used in combination.

The germanium compound being liquid at an ambient temperature may be an inorganic germanium compound or an organic germanium compound. Preferably, it is a germanium tetrahalide or a tetraalkoxygermanium.

Examples of the germanium tetrahalide include $GeBr_4$ (germanium tetrabromide), $GeCl_4$ (germanium tetrachloride) and $GeI_4$ (germanium tetraiodide) (Ge represents a germanium atom).

Examples of an alkoxy group constituting the tetraalkoxygermanium include $Ge(OCH_3)_4$ (tetramethoxygermanium) $Ge(OC_2H_5)_4$ (tetraethoxygermanium), $Ge(O-i-C_3H_7)_4$ (tetra-i-propoxygermanium), $Ge(O-n-C_3H_7)_4$ (tetra-n-propoxygermanium), $Ge(O-i-C_4H_9)_4$ (tetra-i-butoxygermanium), $Ge(O-n-C_4H_9)_4$ (tetra-n-butoxygermanium), $Ge(O-sec-C_4H_9)_4$ (tetra-sec-butoxygermanium), and $Ge(O-t-C_4H_9)_4$ (tetra-t-butoxygermanium).

It is preferred that a seed crystal is placed in the crystal growing vessel and immersed in the melt. The form of the seed crystal is not limited, however, the seed crystal is preferably in the form of a seed crystal film deposited on a supporting substrate.

A material of the supporting substrate is not limited. Nevertheless, examples thereof include sapphire, an AlN template, a GaN template, a GaN self-supporting substrate, a silicon single crystal, a SiC single crystal, an MgO single crystal, spinel ($MgAl_2O_4$), $LiAlO_2$, $LiGaO_2$, and a perovskite-type mixed oxide, such as $LaAlO_3$, $LaGaO_3$, and $NdGaO_3$. Also, it is possible to use a perovskite-type mixed oxide of a cubic crystal system represented by a composition formula $[A_{1-y}(Sr_{1-x}Ba_x)_y][(Al_{1-z}Ga_z)_{1-u}.D_u]O_3$ (where A is a rare-earth element; D is one or more elements selected from the group consisting of niobium and tantalum; y=0.3 to 0.98; x=0 to 1; z=0 to 1; u=0.15 to 0.49; and x+z=0.1 to 2). Further, SCAM ($ScAlMgO_4$) can also be used.

A method for producing the seed crystal film is not particularly limited, however, examples thereof include the vapor phase methods, such as a metal organic chemical vapor deposition (MOCVD) method, a hydride vapor phase epitaxy (HYPE) method, a pulse excited deposition (PXD) method, an MBE method, and a sublimation method, and the liquid phase methods, such as a flux method. Further, as a material of the seed crystal film, the group 13 element nitride is preferable and gallium nitride and gallium aluminum nitride are particularly preferable.

In the present invention, the melt containing the group 13 element source, the flux, and the additive is formed by heating and pressurizing the crystal growing vessel under the nitrogen atom-containing gas atmosphere, and then the group 13 element nitride crystal is grown in the melt.

During this process, a means that prevents evaporation of the additive is used until the flux is melted. There is no particular limitation on such a means as long as it can prevent evaporation of the additive in the crystal growing vessel. For example, the evaporation preventing means may be taken out from the crystal growing vessel to the outside when the flux is melted.

However, in a preferred embodiment, the evaporation preventing means is formed by a shielding object made of the flux. In this embodiment, when the shielding object is melted, the additive is mixed into the melt and the evaporation preventing effect by the shielding object is lost. Thus, it is unnecessary to perform an operation, such as taking out the evaporation preventing means from the outside. Further, the shielding object made of the flux object does not cause crystal impurities, thus it is preferable.

In a preferred embodiment, the shielding object made of the flux constitutes the whole or a part of the container storing the additive.

That is, the whole container can be formed by the shielding object made of the flux. This configuration is preferable in that no unnecessary substances are contaminated or no foreign matters are left in the melt after the container is melted. For example, a container 1 in FIG. 1(a) includes a main body 2 having a storage part 3, and a lid 4. An inner space 3 stores a liquid additive 5 and is sealed by the lid. The reference numeral 6 is a gap.

It is noted that a three-dimensional form of the container is not particularly limited. For example, the main body 2 formed in a rectangular parallelepiped shape shown in FIG. 1(b) or a main body 2A formed in a cylindrical shape shown in FIG. 1(c) may be used.

Figure 2A:
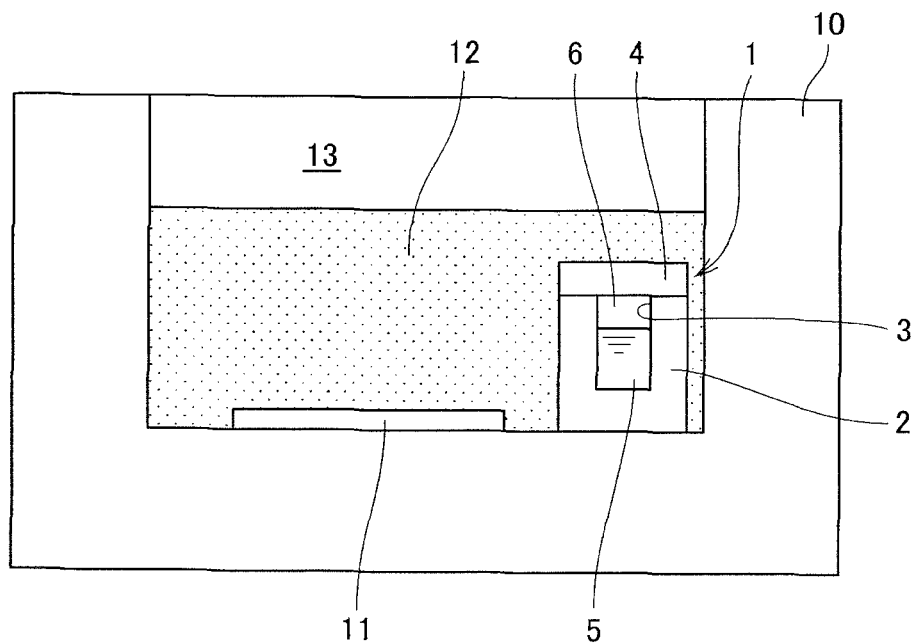
FIG. 2 (a) is a schematic view illustrating a crystal growing vessel 10 in which materials 12 to be melted, a seed crystal substrate 11, and the container 1 are placed.
FIG. 2(b) is a schematic view illustrating the crystal growing vessel 10 in which a melt 14 is formed.

As shown in FIG. 2(a), the prescribed materials 12 to be melted, the seed crystal substrate 11 and the container 1 are placed in an inner space 13 of the prescribed crystal growing vessel 10. In the present example, as described above, the additive 5 is stored in the container 1 and the container 1 is sealed by the main body 2 and the lid 4, both made of the flux. The materials 12 to be melted contain at least the group 13 element source. Since the flux is also supplied from the vessel, the additional flux is charged into the materials 12 for complementing deficiencies in the amount of the flux that is not sufficient only from the weight of the container. Further, desired various kinds of materials may be added into the materials to be melted.

In this state, the inner space of the crystal growing vessel is heated and pressurized to melt the materials to be melted. During this process, first, the flux constituting the container 1 and the flux in the materials 12 are melted and the container 1 is disappeared. The shape of the container 1 remains intact until the flux is melted, thus evaporation of the additive in the container can be prevented. Once the flux is melted, the additive in the container is mixed with the materials 12 to be melted and dissolved therein as the materials to be melted is melted.

Figure 2B:
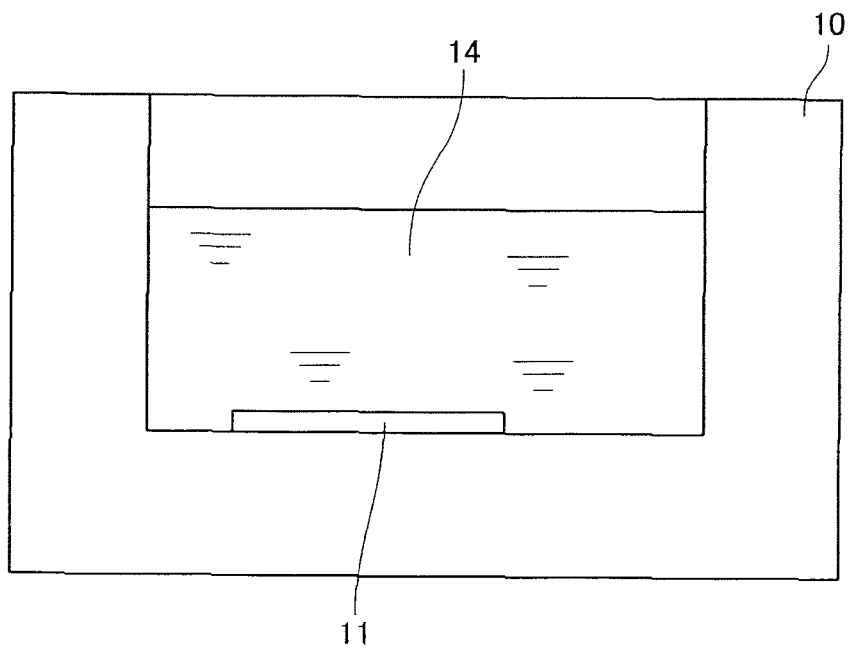

As a result, as shown in FIG. 2(b), a melt 14 is formed in the crystal growing vessel 10 and the seed crystal substrate 11 is immersed in the melt. Then, the group 13 element nitride crystals grow on the seed crystal substrate under the prescribed temperature and pressure conditions. In the melt 14, the group 13 element, the flux, and the additive are mixed.

A method for forming the storage part (a recessed part) in the container made of the flux is not limited. For example, the recessed part may be formed by pressing a projection to the flux. The storage part may be formed by assembling small flux parts. The recessed part may be formed by pouring the molten metal flux into a mold.

Figure 3A:
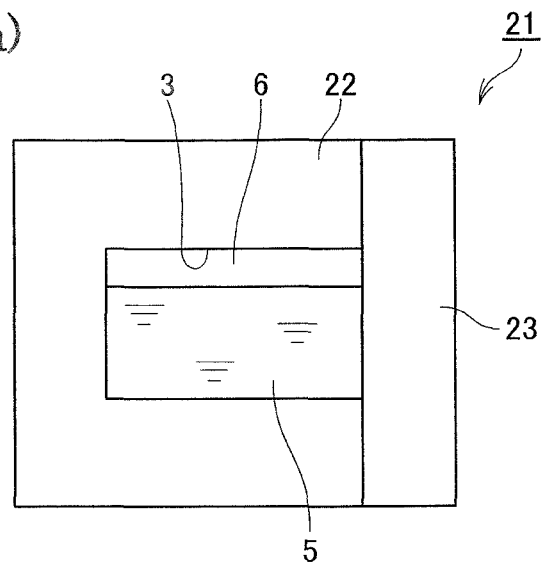
FIGS. 3 (a) and 3(b) are cross-section views schematically illustrating containers 21 and 21A, respectively, each storing an additive.

Further, in a preferred embodiment, the container includes a main body having the storage part having the recessed part that stores the additive, and a lid formed by the shielding object made of the flux. For example, in a container 21 shown in FIG. 3(a), the main body 22 is formed into a bottomed cylindrical shape and a storage part 3 is formed inside the main body 22. Further, a lid 23 is provided inside the main body 22 and the additive 5 is stored inside the container 21.

Figure 4A:
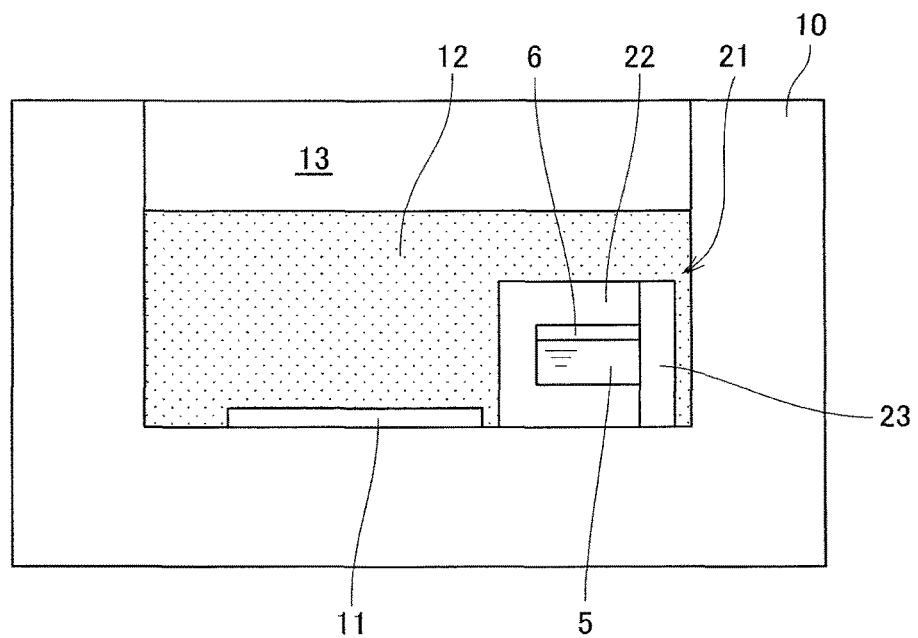
FIG. 4 (a) is a schematic view illustrating the crystal growing vessel 10 in which the materials 12 to be melted, the seed crystal substrate 11, and the container 21 are placed.
FIG. 4(b) is a schematic view illustrating the crystal growing vessel 10 in which the melt 14 is formed.

Further, as shown in FIG. 4(a), the materials 12 to be melted, the seed crystal substrate 11 and the container 21 are placed in the inner space 13 of the crystal growing vessel 10. The materials 12 to be melted contain at least the group 13 element source. Since the flux is also supplied from the lid 23, the additional flux is charged into the materials 12 for complementing deficiencies in the amount of the flux that is not sufficient only from the weight of the lid 23.

In this state, the inside of the crystal growing vessel is heated and pressurized to melt the materials to be melted. During this process, first, the flux constituting the lid 23 of the container and the flux in the materials 12 are melted and the lid 23 is disappeared. The shape of the container remains intact until the flux is melted, thus evaporation of the additive 5 in the container can be prevented. Once the flux is melted, the additive in the container is mixed with the materials 12 to be melted and dissolved therein as the materials to be melted are melted.

Figure 4B:
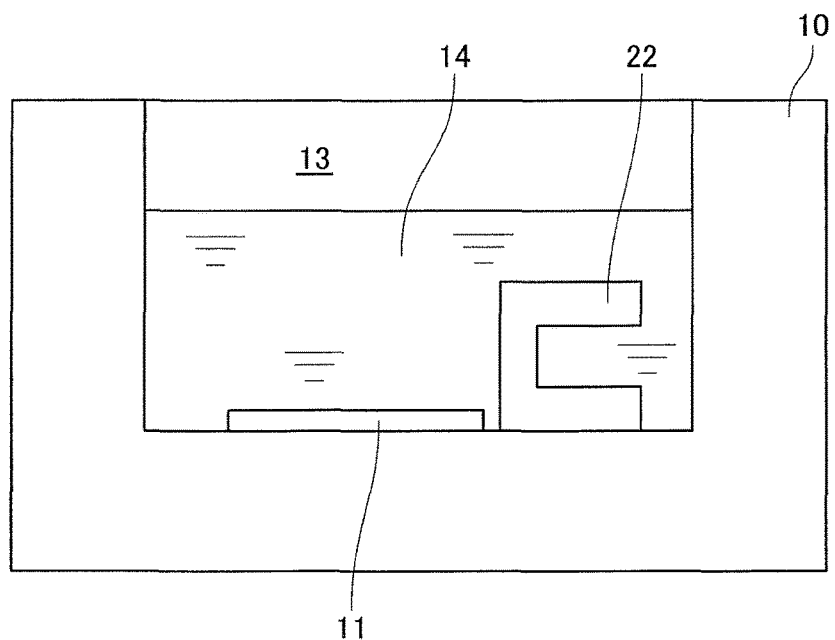

As a result, as shown in FIG. 4(b), the melt 14 is formed in the crystal growing vessel 10 and the seed crystal substrate 11 and the container main body 22 are immersed in the melt. Then, the group 13 element nitride crystals grow on the seed crystal substrate under the prescribed temperature and pressure conditions. In the melt 14, the group 13 element, the flux, and the additive are mixed.

Further, in the present embodiment, as shown in FIG. 4(a), an opening of the storage part covered with the lid 23 faces arranged preferably in a horizontal direction or oblique direction, so that the additive 5 in the container can easily flow out when the lid is melted.

Further, in a preferred embodiment, the container includes a cylindrical part that stores the additive and a pair of lids formed by the shielding object.

Figure 3B:
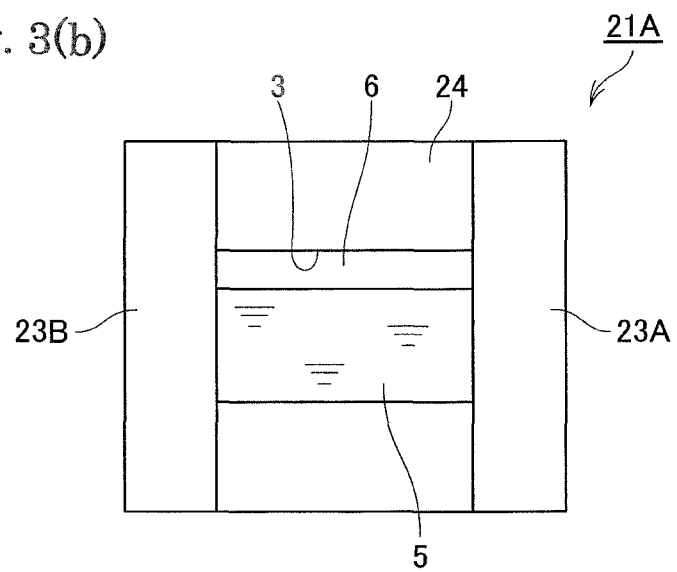

For example, in a vessel 21A shown in FIG. 3(b), a main body 24 is formed in a cylindrical shape and the storage part is formed in the main body 24. Then, a pair of lids 23A and 23B is provided on the main body 24 and the additive 5 is stored in the vessel 21A.

Figure 5A:
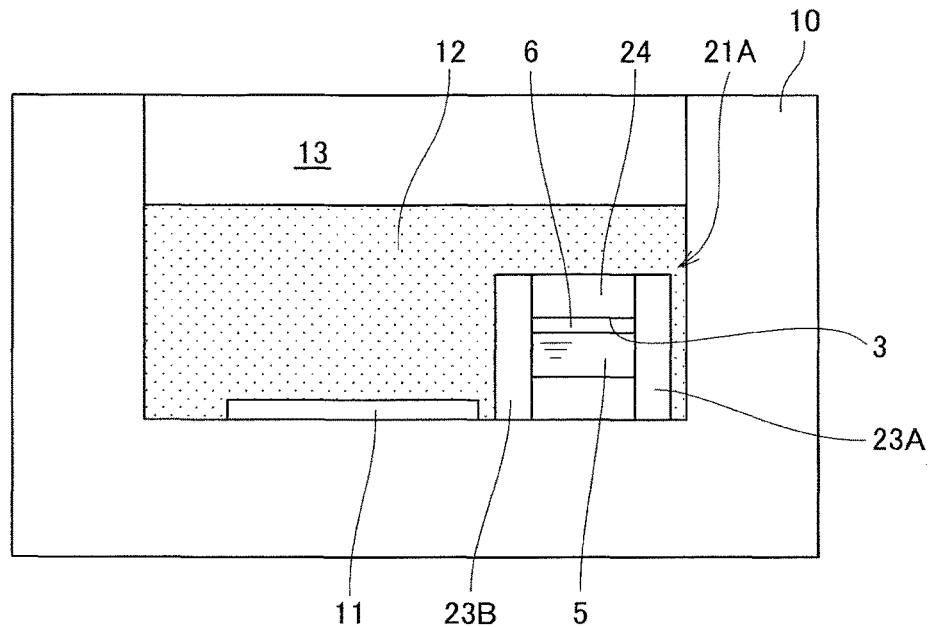
FIG. 5 (a) is a schematic view illustrating the crystal growing vessel 10 in which the materials 12 to be melted, the seed crystal substrate 11, and the container 21A are placed and, FIG. 5(b) is a schematic view illustrating the crystal growing vessel 10 in which the melt 14 is formed.

Then, as shown in FIG. 5(a), the materials 12 to be melted, the seed crystal substrate 11, and the container 21A are placed in the inner space 13 of the crystal growing vessel 10. The materials 12 to be melted contain at least the group 13 element source. Since the flux is also supplied from the lids 23A and 23B, the additional flux is charged into the materials 12 for complementing deficiencies in the amount of the flux that is not sufficient only from the weight of the lids.

In this state, the inside of the crystal growing vessel is heated and pressurized to melt the materials to be melted. During this process, first, the flux constituting the lids 23A and 23B of the container and the flux in the materials 12 are melted and the lids are disappeared. The shape of the container remains intact until the flux is melted, thus evaporation of the additive in the container can be prevented. Once the flux is melted, the additive in the container is mixed with the materials 12 to be melted and dissolved therein as the materials to be melted are melted.

Figure 5B:
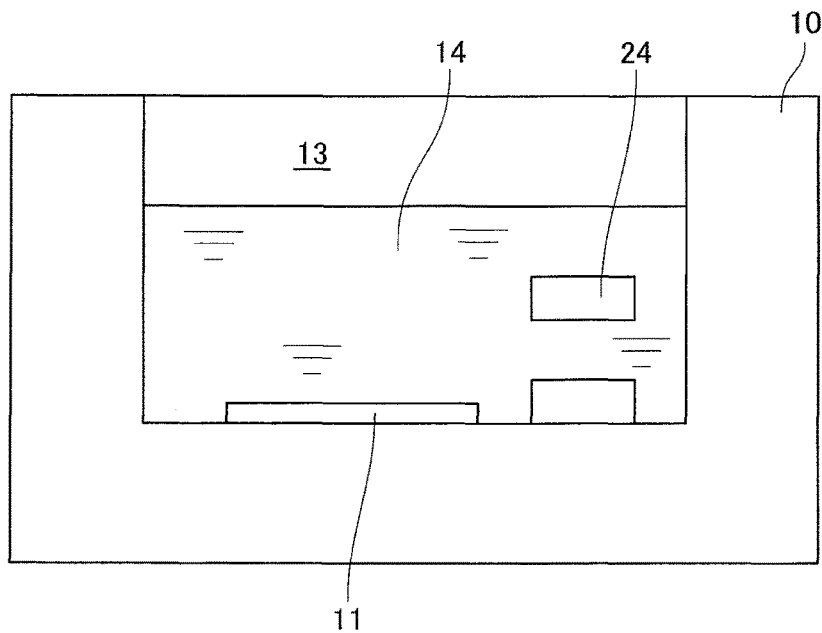

As a result, as shown in FIG. 5(b), the melt 14 is formed in the crystal growing vessel 10, and the seed crystal substrate 11 and the vessel main body 24 having a cylindrical shape are immersed in the melt. Then, the group 13 element nitride crystals grow on the seed crystal substrate under the prescribed temperature and pressure conditions. In the melt 14, the group 13 element, the flux, and the additive are mixed.

Further, in the present embodiment, as shown in FIG. 5(a), openings of the storage part covered with the lids 23A and 23B face preferably in a horizontal direction or oblique direction, so that the additive in the container can easily flow out when the lids are melted. In particular, the outflow of the additive inside the container to the outside is facilitated by providing the plurality of the lids.

It is preferred that a material of the main bodies 22 or 24 is not dissolved in the melt or it does not have an adverse effect even if dissolved in the melt. Examples of such a material include a dense ceramic, such as aluminum nitride, aluminum oxide, silicon nitride. yttrium oxide, and yttrium aluminum garnet. Further, a polymer compound, such as a synthetic resin, including polyethylene, polypropylene, and polyurethane, and a polysaccharide, including cellulose, amylose, and amylopectin, can be used.

Further, an external shape of the container may be various shapes, such as a cylindrical shape, a rectangular parallelepiped shape, and a spherical shape.

Further, in a preferred embodiment, the storage part that stores the additive is provided in the crystal growing vessel and the shielding object is arranged between the storage part and the inner space of the crystal growing vessel.

Figure 6A:
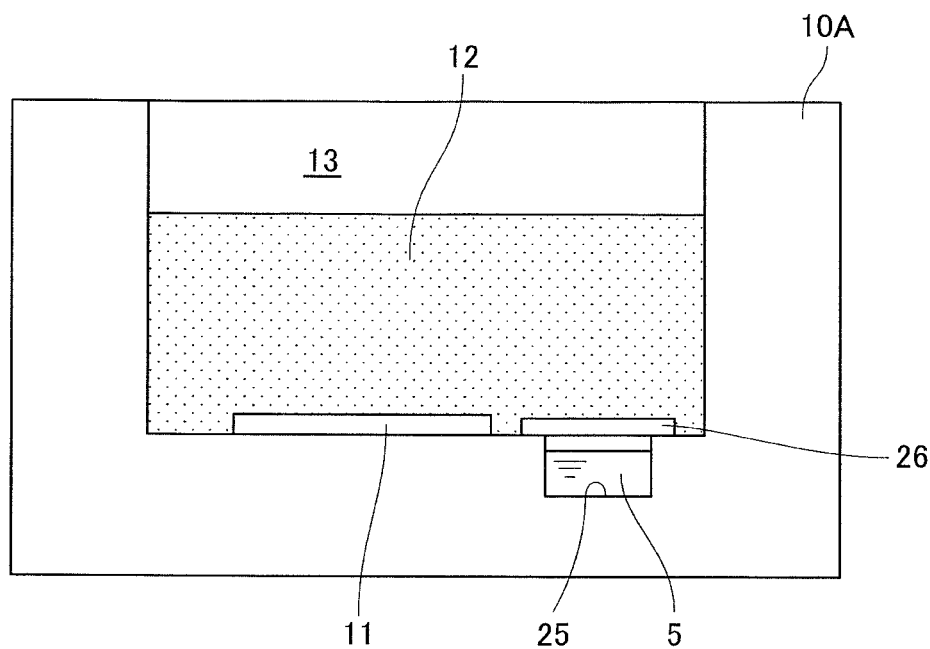
FIG. 6 (a) is a schematic view illustrating a crystal growing vessel 10A in which the materials 12 to be melted and the seed crystal substrate 11 are placed and a storage part 25 in which an additive 5 is stored.
FIG. 6(b) is a schematic view illustrating the crystal growing vessel 10A in which the melt 14 is formed.

For example, as shown in FIG. 6(a), a storage part 25 is formed in the prescribed crystal growing vessel 10A, and the storage part 25 and the inner space 13 are mutually communicated. Further, the additive 5 is stored in the storage part 25 of the crystal growing vessel 10A and the storage part 25 is covered with a shielding object 26 made of the flux. Then, the prescribed materials 12 to be melted and seed crystal substrate 11 are placed in the inner space 13 of the crystal growing vessel 10A. The materials 12 to be melted contain at least the group 13 element source. Since the flux is also supplied from the shielding object 26, the additional flux is charged into the materials 12 for complementing deficiencies in the amount of the flux that is not sufficient only from the weight of the shielding object 26.

In this state, the inside of the crystal growing vessel is heated and pressurized to melt the materials to be melted. During this process, first, the flux constituting the shielding object 26 and the flux in the materials 12 are melted and the shielding object 26 is disappeared. The shape of the shielding object remains intact until the flux is melted, thus evaporation of the additive 5 in the storage part 25 can be prevented. Once the flux is melted, the additive is mixed with the materials 12 to be melted and dissolved therein as the materials to be melted are melted.

Figure 6B:
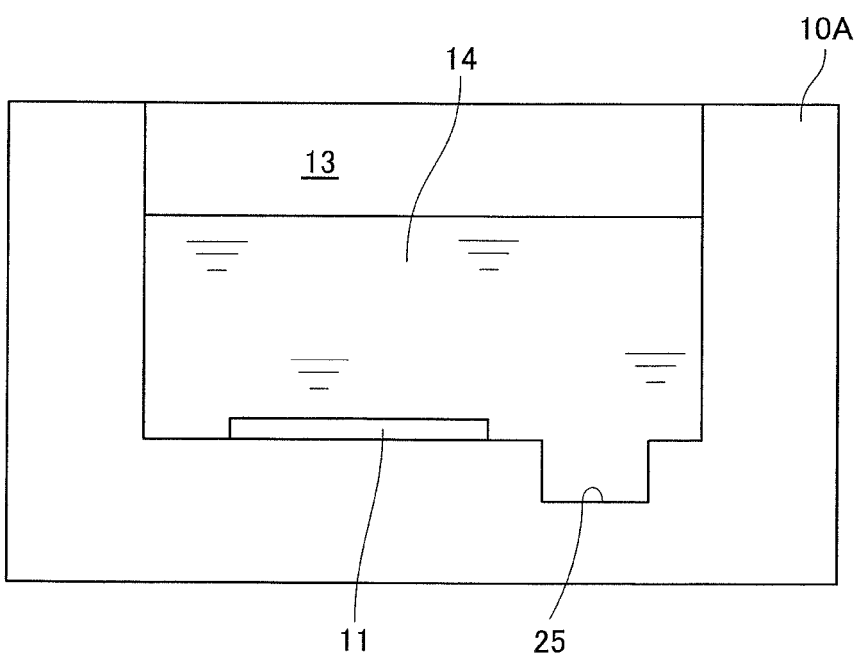

As a result, as shown in FIG. 6(b), the melt 14 is formed in the crystal growing vessel 10 and the seed crystal substrate 11 is immersed in the melt. Then, the group 13 element nitride crystals grow on the seed crystal substrate under the prescribed temperature and pressure conditions. In the melt 14, the group 13 element, the flux, and the additive are mixed.

Further, the additive may be stored in a container made of an organic compound and the vessel may be placed in the crystal growing vessel. In this case, an adhesion part of the vessel may be detached by heating to release the additive in the container. As the organic compound to be used, a polymer compound is preferable from the standpoint of easiness in adhesion work, and a synthetic resin, such as polyethylene, polypropylene and polyurethane, and a polysaccharide, such as cellulose, amylose, and amylopectin, can be used.

In a preferred embodiment, the crystal growing vessel storing the flux is placed in a pressure vessel and heated under the high pressure. During this process, atmosphere gas containing nitrogen-atom containing gas is compressed to a prescribed pressure and supplied into the pressure vessel to control the total pressure and a partial pressure of the nitrogen atom-containing gas in the pressure vessel.

The heating temperature and pressure during the growth step of the group 13 element nitride crystals are selected based on a composition and crystal structure of the single crystal to be grown, thus they are not particularly limited. The heating temperature may be set to, for example, 800 to 1500° C. The heating temperature is set to further preferably 850° C. or higher. Further, the heating temperature is set to preferably 800 to 1200° C., further preferably 800 to 1100° C.

The nitrogen atom-containing gas is preferably nitrogen gas, however, it may be ammonia. The pressure of the nitrogen atom-containing gas is not particularly limited, but it is preferably 1 MPa or higher, further preferably 2 MPa or higher. The upper limit of the pressure of the nitrogen atom-containing gas is not particularly limited, however, it may be set to, for example, 200 MPa or lower, preferably 100 MPa or lower.

In a preferred embodiment, the pressurization is initiated before the flux is melted. This configuration is more preferable since evaporation of the molten flux is suppressed by the pressurization. From this standpoint, the pressure when the flux is melted is set to preferably 1 MPa or higher, further preferably 2 MPa or higher. Further, the ratio of (the pressure when the flux is melted/the pressure when the crystals are grown) is set to preferably 0.2 to 1, further preferably 0.3 to 1.

There is no limitation to gas other than the nitrogen atom-containing gas in the atmosphere, however, inert gas is preferable, and argon, helium, and neon are particularly preferable. A partial pressure of the gas other than the nitrogen atom-containing gas is obtained by subtracting the partial pressure of the nitrogen atom-containing gas from the total pressure.

EXAMPLES

Example 1

Gallium nitride crystals were grown according to the method described while referring to FIG. 1 and FIG. 2.

Figure 1B:
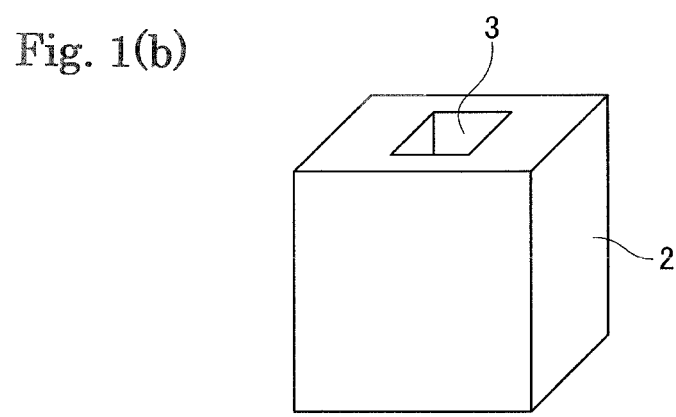
Figure 1C:
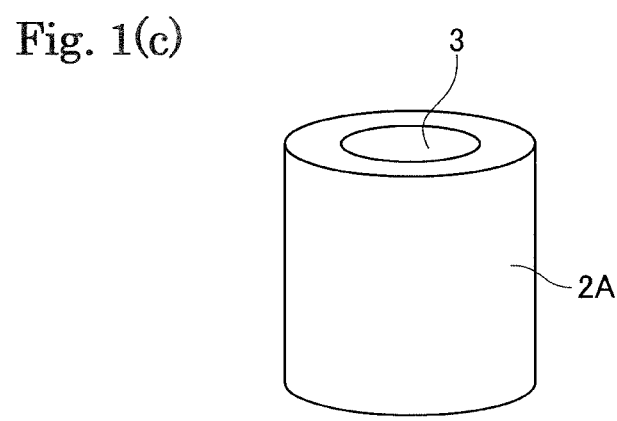

Specifically, a main body 2 as shown in FIGS. 1(a) and (b) was formed from sodium metal having a purity of 99.95 wt %, and 25 mg of hexane as a hydrocarbon was placed in a recessed part 3 of the main body 2. The main body 2 was sealed by a lid 4 made of the sodium metal having a purity of 99.95 wt %.

In a glove box containing an argon atmosphere, 30 g of gallium (Ga) metal having a purity of 99.9999 wt %, the sodium (Na) metal having a purity of 99.95 wt %, the main body 2 and the lid 4 by which the hydrocarbon was sealed, and a seed crystal substrate 11 having a diameter of 2 inches were placed in a crystal growing vessel 10. The total amount of the sodium metal was adjusted to 40 g.

In this example, the seed crystal substrate 11 was formed by depositing a seed crystal film made of the gallium nitride crystals on a supporting substrate made of sapphire by the MOCVD method.

Next, a lid was placed on the crystal growing vessel. They were sealed in a stainless-steel vessel, taken out from the glove box, and transferred to a growth apparatus. The crystal growth was performed under the growth conditions of a nitrogen pressure of 4.5 MPa and an average temperature of 875° C.

Then, after crucibles were cooled down to 25° C. by taking 10 hours, the crucibles were recovered. Residues of the growth materials were removed by using ethanol and the crystals were recovered.

The obtained GaN crystals were clear and colorless. The growth rate of the GaN crystals was 3.0 microns/hr±0.2 microns/hr with less variation. Further, there were no cracks in any of 10 samples produced in this manner.

Example 2

The GaN crystals were grown in the same manner as in Example 1. However, in the present example, the container 21, which was described while referring to FIG. 3(a) and FIG. 4, was used. Specifically, the main body 22 was formed by aluminum oxide having a purity of 99.6%, and the lid 23 was formed by sodium metal. The GaN crystals were grown in the same manner as in Example 1 except for the above.

The obtained GaN crystals were clear and colorless. The growth rate of the GaN crystals was 3.0 microns/hr±0.2 microns/hr with less variation. Further, there were no cracks in any of 10 samples produced in this manner.

Example 3

The GaN crystals were grown in the same manner as in Example 1. However, in the present example, the container having a shape described while referring to FIGS. 1(a) and (b) was used. It is noted that the material of the container was a polymer compound (polyethylene), and a hydrocarbon was stored in the container and the container was sealed by adhesion. The GaN crystals were grown in the same manner as in Example 1 except for the above.

The obtained GaN crystals were clear and colorless. The growth rate of the GaN crystals was 3.0 microns/hr±0.3 microns/hr with less variation. Further, the cracks were found in 1 out of 10 samples produced in this manner.

Example 4

The GaN crystals were grown in the same manner as in Example 1. However, in the present example, 1.85 g of germanium tetrachloride (the ratio with respect to Ga metal: 2.0 mol %) was added instead of hexane. The GaN crystals were grown in the same manner as in Example 1 except for the above.

The obtained GaN crystals were clear and colorless. The growth rate of the GaN crystals was 2.5 microns/hr±0.2 microns/hr The carrier concentration measured by the Hall measurement was $3.0 \times 10^{18}/cm^3$.

Variation in the carrier concentrations obtained from 5 tests conducted under the same conditions was $3.0 \pm 0.3 \times 10^{18}/cm^3$.

Comparative Example 1

The GaN crystals were grown in the same manner as in Example 1. However, in the present example, 140 mg of the hydrocarbon was charged into the materials 12 to be melted in advance, and the evaporation preventing means for the hydrocarbon was not provided. The GaN crystals were grown in the same manner as in Example 1 except for the above.

The obtained GaN crystals were clear and colorless. The growth rate of the GaN crystals was 5.5 microns/hr±1.5 microns/hr. Further, the cracks were found in 6 out of 10 samples produced in this manner.

Comparative Example 2

The GaN crystals were grown in the same manner as in Example 1. However, in the present example, 4 g of germanium tetrachloride was added instead of hexane without providing the evaporation preventing means for germanium tetrachloride. The GaN crystals were grown in the same manner as in Example 1 except for the above.

The obtained GaN crystals were clear and colorless. The growth rate of the GaN crystals was 2.5 microns/hr±0.2 microns/hr The carrier concentration measured by the Hall measurement was $1.8 \times 10^{18}/cm^3$.

Variation in the carrier concentrations obtained from 5 tests conducted under the same conditions was $1.5\pm0.8\times10^{18}/cm^3$.

The invention claimed is:

1. A method of producing a crystal of a nitride of a group 13 element, said method comprising:

placing a group 13 element source, a flux comprising at least one of an alkali metal and an alkaline earth metal, and an additive being liquid at an ambient temperature in a crystal growing vessel; and heating and pressurizing said crystal growing vessel under a nitrogen atom-containing gas atmosphere to form a melt containing said group 13 element source, said flux and said additive, wherein evaporation of said additive is prevented by a shielding object consisting essentially of said flux until said flux is melted and then said crystal of said nitride of said group 13 element is grown in said melt, wherein said additive is hydrocarbon or a dopant of said crystal;

wherein said additive is contained in a container; and wherein the whole of said container is composed of said shielding object and is dissolved into said melt, or wherein said container comprises a main body having a storage part storing said additive and a lid composed of said shielding object, and said lid is dissolved into said melt and said main body is left in said melt.

2. The method of claim 1, wherein said main body comprises a cylindrical part and said lid comprises a pair of said lids each consisting essentially of said shielding object.

3. The method of claim 1, wherein said pressurization is initiated before said flux is melted.

4. The method of claim 1, wherein said additive comprises a hydrocarbon.

5. The method of claim 1, wherein a boiling point of said additive is equal to or lower than a melting point of said flux.

6. A crystal growth apparatus of growing a crystal of a nitride of a group 13 element, wherein a group 13 element source, a flux comprising at least one of an alkali metal and an alkaline earth metal, and an additive being liquid at an ambient temperature are placed in a crystal growing vessel; and wherein said crystal growing vessel is heated and pressurized under a nitrogen atom-containing gas atmosphere to form a melt containing said group 13 element source, said flux and said additive to grow said crystal of said nitride of said group 13 element in said melt, wherein said additive is hydrocarbon or a dopant of said crystal, said apparatus comprising an evaporation preventing means for preventing evaporation of said additive until said flux is melted in a process of heating and pressurizing said crystal growing vessel, wherein said evaporation preventing means comprises a shielding object consisting essentially of said flux, wherein said additive is contained in a container, and wherein the whole of said container is composed of said shielding object and is dissolved into said melt, or wherein said container comprises a main body having a storage part storing said additive and a lid composed of said shielding object, and said lid is dissolved into said melt and said main body is left in said melt.

7. The apparatus of claim 6, wherein said main body comprises a cylindrical part and said lid comprises a pair of said lids each consisting essentially of said shielding object.

8. The apparatus of claim 6, wherein said additive comprises a hydrocarbon.

9. The apparatus of claim 6, wherein a boiling point of said additive is equal to or lower than a melting point of said flux.

10. A method of producing a crystal of a nitride of a group 13 element, said method comprising:

placing a group 13 element source, a flux comprising at least one of an alkali metal and an alkaline earth metal, and an additive being liquid at an ambient temperature in a crystal growing vessel; and heating and pressurizing said crystal growing vessel under a nitrogen atom-containing gas atmosphere to form a melt containing said group 13 element source, said flux and said additive, wherein evaporation of said additive is prevented by a shielding object consisting essentially of said flux until said flux is melted and then said crystal of said nitride of said group 13 element is grown in said melt, wherein said additive is hydrocarbon or a dopant of said crystal, wherein said crystal growing vessel comprises a storage part storing said additive, wherein said shielding object is arranged between said storage part and an inner space of said crystal growing vessel, and wherein said shielding object is dissolved into said melt so that said storage part and said inner space are communicated with each other.

11. A crystal growth apparatus of growing a crystal of a nitride of a group 13 element, wherein a group 13 element source, a flux comprising at least one of an alkali metal and an alkaline earth metal, and an additive being liquid at an ambient temperature are placed in a crystal growing vessel; and wherein said crystal growing vessel is heated and pressurized under a nitrogen atom-containing gas atmosphere to form a melt containing said group 13 element source, said flux and said additive to grow said crystal of said nitride of said group 13 element in said melt, wherein said additive is hydrocarbon or a dopant of said crystal, said apparatus comprising an evaporation preventing means for preventing evaporation of said additive until said flux is melted in a process of heating and pressurizing said crystal growing vessel, wherein said evaporation preventing means comprises a shielding object consisting essentially of said flux, wherein said crystal growing vessel comprises a storage part storing said additive, wherein said shielding object is arranged between said storage part and an inner space of said crystal growing vessel, and wherein said shielding object is dissolved into said melt so that said storage part and said inner space are communicated with each other.

* * * * *